(12) United States Patent
Ratner et al.

(10) Patent No.: US 7,480,047 B1
(45) Date of Patent: Jan. 20, 2009

(54) TIME-DOMAIN COMPUTATION OF SCATTERING SPECTRA FOR USE IN SPECTROSCOPIC METROLOGY

(75) Inventors: Edward Ratner, Sunnyvale, CA (US); Andrei Veldman, Issaquah, WA (US); Daniel Wack, Los Altos, CA (US)

(73) Assignee: KLA-Tencor Corporation, San Jose, CA (US)

( * ) Notice: Subject to any disclaimer, the term of this patent is extended or adjusted under 35 U.S.C. 154(b) by 284 days.

(21) Appl. No.: 11/320,191

(22) Filed: Dec. 28, 2005

(51) Int. Cl.
*G01J 3/28* (2006.01)
*G01J 4/00* (2006.01)
(52) U.S. Cl. ...................... 356/326; 356/369
(58) Field of Classification Search ............. 356/326, 356/364–369
See application file for complete search history.

(56) References Cited

U.S. PATENT DOCUMENTS 6,574,650 B1* 6/2003 Aoki .......................... 708/446
2005/0105787 A1* 5/2005 Gulati ........................ 382/129

OTHER PUBLICATIONS

Gedney et al, Computational Electrodynamics: The Finite-Difference Time-Domain Method, Sections 7.1-7.3 and 9.5-9.5.2, Artech House Publishers, Jun. 2000.

* cited by examiner

*Primary Examiner*—Tarifur Chowdhury
*Assistant Examiner*—Tara S Pajoohi
(74) *Attorney, Agent, or Firm*—Luedeka, Neely & Graham, P.C.

(57) ABSTRACT

In an embodiment, a method of time-domain simulation for simulating scattering spectra is described. The method may provide for computing spatial derivatives including computing spectral derivatives in some portion of the domain and finite difference derivatives in some other portion of the domain; forming an equation for non-reflecting boundary conditions; and computing a time-stepping scheme using a high-order unconditionally stable computation method.

28 Claims, 3 Drawing Sheets

```
┌─────────────────────────┐
│   Add Absorbing Layer to │
│ Computational Domain or Solve │
│       Wave Equation      │
│           402            │
└─────────────────────────┘
```

*FIG. 4*

```
┌─────────────────────────┐
│ Compute Time-Step Using High-│
│  Order Unconditionally Stable│
│     Computation Method   │
│           502            │
└─────────────────────────┘
```

*FIG. 5*

TIME-DOMAIN COMPUTATION OF SCATTERING SPECTRA FOR USE IN SPECTROSCOPIC METROLOGY

BACKGROUND

The subject matter described herein generally relates to a system and method for time-domain simulation. More specifically, an embodiment relates to time-domain computation of scattering spectra (e.g., electromagnetic (EM) spectra) for use in spectroscopic metrology.

Time-domain simulation has been used to compute scattering properties. Typically, a scattering geometry is given from which transmission and reflection coefficients are computed, as well as their associated phases.

Typical optical systems have a finite spatial width for the apertures used to produce the light incident on the scatterer, and define the range of collection angles. In order to accurately model the scattering process, it may be necessary to model the finite spread of incident angles.

The problem has traditionally been solved in the time-domain by performing the scattering computation for a fixed set of angles that samples the finite angular spread of the aperture. The reflection and transmission spectra are then computed as a weighted average of the spectra of the spectra obtained at each incident angle. Unfortunately, the computational load grows linearly with the number of angle samples used. Hence, for high accuracy work, e.g., required in scatterometry, 3 to 9 incident angles may be used, resulting in a factor of 3 to 9 increase in the computational time.

SUMMARY

Embodiments of the present invention provide systems and methods for efficiently truncating the computational domain using a non-reflecting boundary condition for dispersive materials. In a time-domain computation using transient wave excitation, the transmission and reflection coefficients for a range of wavelengths may be obtainable with one scattering simulation or "run." A broadband pulse may be composed of a combination of plane-waves spanning the frequencies of interest, all traveling in the same direction. The simulation may be run from the time the broadband pulse is incident on the scatterer until the outgoing waves have diminished to a desired threshold level. The outgoing waveforms in the directions of interest may be Fourier transformed and the ratio of intensities between the incident and outgoing waveforms for each of the Fourier components may result in estimates of the transmission and reflection coefficients.

In an embodiment, a linear combination of plane waves for the incident pulse may be utilized to simulate a finite aperture for the incident beam in a single time-domain solution. Further, the present invention may use a "stitched" domain technique where the derivative in one part of the domain is computed using finite differences and spectral method in the other. In the transition region, the derivative may be a linear combination of the two techniques. Such an embodiment may use a high-order unconditionally stable time-stepping method which is both stable and accurate for large time-steps.

In one embodiment, a scattering spectrum (e.g., EM scattering spectrum) may be obtained for a finite width aperture in one time-domain simulation. An incident pulse may be synthesized that has a desired range of wavelengths as well as a desired range of angles. The scattering spectrum may be calculated using a single time-domain scattering calculation. This may have the same computational cost as a scattering calculation for a single incident angle. Accordingly, as many sample angles as practical may be included in the computation.

Since the light coming through the aperture may be spatially incoherent, a Monte Carlo-like technique may be used, where each of the components corresponding to different sample angles has a different, randomly generated phase $\phi_j$. The incident pulse is given by:

$$\sum_{\vartheta_j} \sum_{\omega_i} A_{ij} \exp(i(\vec{k}_{ij} \cdot \vec{x} - \omega_i t + \varphi_j)) \text{ where } \vec{k}_{ij} = |k_i|\cos\vartheta_j \hat{x} + |k_i|\sin\vartheta_j \hat{y}.$$

The transmission and reflection spectra may be calculated in the standard fashion along the direction of interest. The averaging that results may correspond to an averaging over a random variable $\phi$, resulting in a spatially incoherent averaging.

The relatively long integration time of the physical detector, as well as the corresponding computation, may result in the accurate approximation of the temporally incoherent source.

With the use of the "random phase" incident pulse, a single time-domain scattering computation may be needed, which results in significantly faster run times for calculations involving finite width apertures.

Additional advantages, objects and features of embodiments of the invention are set forth in part in the detailed description which follows. It is to be understood that both the foregoing general description and the following detailed description are merely exemplary of embodiments of the invention, and are intended to provide an overview or framework for understanding the nature and character of embodiments of the invention.

BRIEF DESCRIPTION OF THE DRAWINGS

The accompanying drawings are included to provide further understanding of embodiments of the invention, illustrate various embodiments of the invention, and together with the description serve to explain the principles and operation of the invention. In the figures, the left-most digit(s) of a reference number identifies the figure in which the reference number first appears. The use of the same reference numbers in different figures indicates similar or identical items.

DETAILED DESCRIPTION

In the following description, numerous specific details are set forth in order to provide a thorough understanding of embodiments of the present invention. Embodiments of the present invention may be practiced without some or all of these specific details. In other instances, well known process operations have not been described in detail in order not to unnecessarily obscure the present invention. Also, reference in the specification to "one embodiment" or "an embodiment" means that a particular feature, structure, or characteristic described in connection with the embodiment may be included in at least an implementation. The appearances of the phrase "in one embodiment" in various places in the specification may or may not be all referring to the same embodiment.

Figure 1:
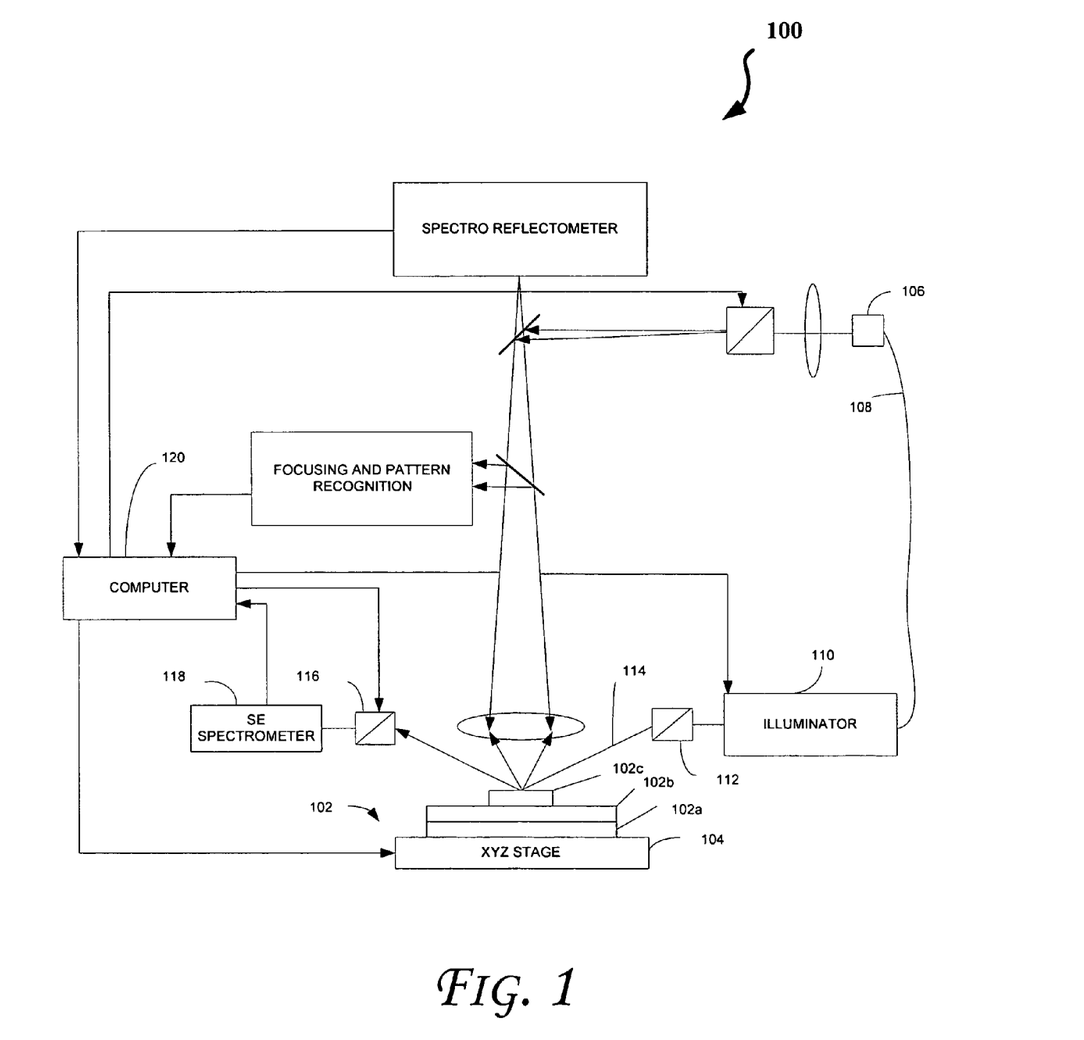
FIG. 1 is a schematic view of an embodiment of a representative spectroscopic scatterometer system.

FIG. 1 is a schematic view of a representative spectroscopic scatterometer system, according to an embodiment. As shown in FIG. 1, a semiconductor wafer may comprise a silicon substrate 102a, a film 102b on the substrate and a diffracting structure 102c such as a photoresist pattern on the film, where the film is at least partially light-transmissive and has a certain film thickness and refractive index (n and k, the real and imaginary components of the index).

Before the diffracting structure 102c is measured, an XYZ stage 104 is used for moving the wafer in the horizontal XY directions in order to first measure the film thickness and refractive index of the underlying structure underneath the photoresist pattern 102c.

For the purpose of measuring the film thickness and refractive index of the underlying structure (102b and 102a), a broadband radiation source such as white light source 106 supplies light through a fiber optic cable 108 which randomizes the polarization and creates a uniform light source for illuminating the wafer. Upon emerging from fiber 108, the radiation passes through an optical illuminator that may include a slit aperture and a focus lens (not shown). The slit aperture causes the emerging light beam to image a small area of layer 102b. The light emerging from illuminator 110 is polarized by a polarizer 112 to produce a polarized sampling beam 114 illuminating the layer 102b.

The radiation originating from sampling beam 114 that is reflected by layer 102b, passed through an analyzer 116 and to a spectrometer 118 to detect different spectral components of the reflected radiation. In the spectroscopic ellipsometry (SE) mode of system 100 for measuring film thickness and refractive index, either the polarizer 112 or the analyzer 114 is rotated (to cause relative rotational motion between the polarizer and the analyzer) when spectrometer 118 is detecting the reflected light at a plurality of wavelengths, such as those in the spectrum of the radiation source 106, where the rotation is controlled by computer 120 in a manner known to those skilled in the art. The reflected intensities at different wavelengths detected is supplied to computer 120 which computes the film thickness and n and k values of the refractive index of layer 102b.

The use of SE in metrology of small structures and/or patterns has gained wide acceptance. The determination of the structure is achieved by starting with a model of the underlying structure, computing the scattered spectrum, comparing the computed spectrum with the obtained measured spectrum and then adjusting the model. This process is repeated until convergence.

In order to maximize the benefit to production lines, the determination of the model should happen as quickly as possible. The result should also be as reliable as possible, meaning that if the same structure is measured multiple times—the models produced should be as similar as possible.

The SE hardware uses a broad-band light source, thus, the collected spectrum may contain a large number of wavelengths, typically on the order of 1000. To increase the reliability of determining the model as many of these wavelengths as possible need to be used. The limiting factor is computational cost of the modeled spectrum. Currently in metrology applications, a frequency domain computational approach may be used—which means that the computational cost scales linearly with the number of wavelengths used. Given fixed computing budgets this leads to use of a small number of wavelengths.

In an embodiment, the present invention provides a technique to compute the scattering spectrum for all the wavelengths as the simulation of a single scattering event. Thus, the computational cost does not grow appreciably as the number of wavelengths used increases.

Figure 2:
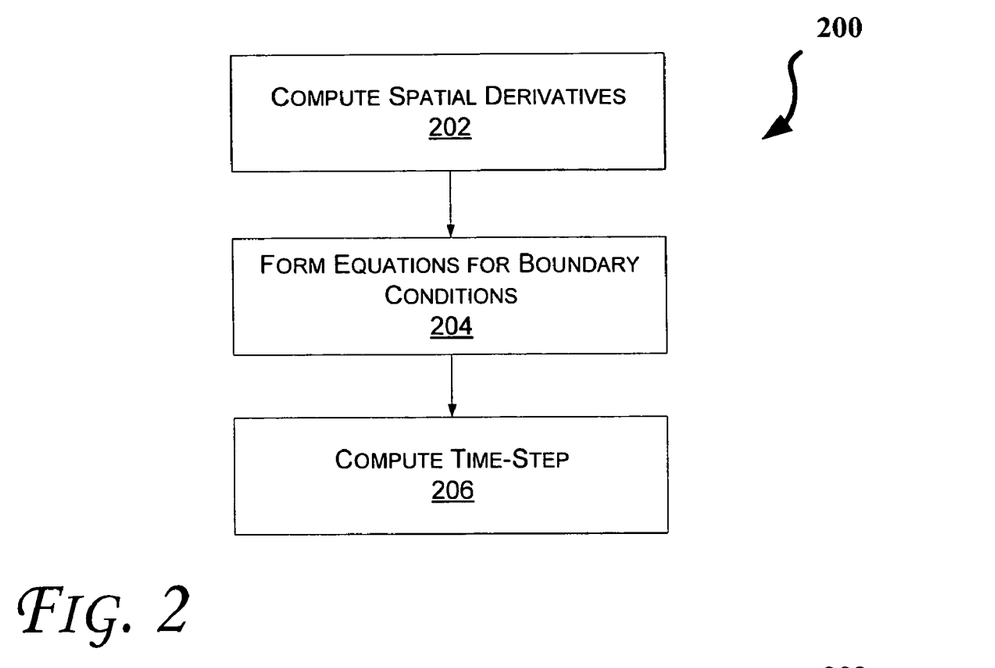
FIG. 2 is a flow diagram of a time step method in accordance with an embodiment of the present invention.

As shown in FIG. 2, to apply embodiments of the present invention to metrology, the method includes truncating the computational domain in a dispersive media and using a single scattering calculation to model the scattering of light (e.g., EM scattering) produced by an aperture of finite width. A further improvement is accomplished by computing spatial derivatives (202) by computing spectral derivatives in some portion of the domain and finite-difference in others, forming non-reflecting equations for boundary conditions (204) and computing high-order unconditionally stable time-stepping schemes with dispersive materials (206).

Total Field/Scattered Field Framework

In one embodiment of the present invention, a spatial derivative domain technique is used where the derivative in one portion of the domain is computed using a spectral method and a finite differences method is used in another portion of the domain. In the transition region, the derivative may be a linear combination of these two techniques.

Figure 3:
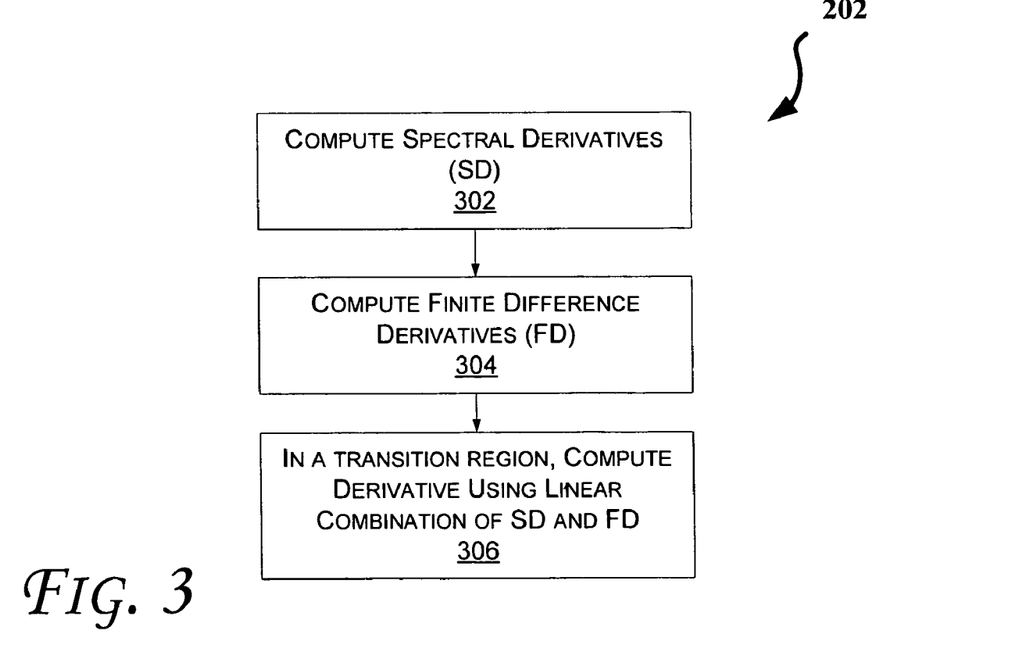
FIGS. 3-5 are flow diagrams of various embodiments of the present invention.

As shown in FIG. 3, the stage 202 includes computing the three derivative types as follows. Let the domain be defined by (1):

$$-N \leq i \leq N$$

For K<N, define the total field domain by (2):

$$-N \leq i \leq K$$

and the scattered field domain by (3):

$$K < i \leq N.$$

Thus, using the following notation (4):

$$H(x_i, t_j) = H_i^j \text{ and } E(x_i, t_j) = E_i^j,$$

the update equations to first order in both time and space are given by (5):

$$E_i^{j+1} = E_i^j + \frac{\Delta t}{2\varepsilon_0 \Delta x}(H_{i+1}^j - H_{i-1}^j).$$

Thus, for i<K operations are with total fields everywhere in the equation, and for i>K+1 operations are with scattered fields. The transition yields the following (6):

$$E_K^{j+1} = E_K^j + \frac{\Delta t}{2\varepsilon_0 \Delta x}(H_{K+1,total}^j - H_{K-1}^j) =$$

$$E_K^j + \frac{\Delta t}{2\varepsilon_0 \Delta x}((H_{K+1}^j + H_{inc}(x_{K+1}, t_i)) - H_{K-1}^j) =$$

$$E_K^j + \frac{\Delta t}{2\varepsilon_0 \Delta x}((H_{inc}(x_{K+1}, t_i) - H_{K-1}^j) + H_{K+1}^j)$$

Operating on the incident and total quantities first and then adding in the scattered field quantities, the scattered field quantities are expected to be smaller when the incident field is impinging.

In the scattered region (7):

$$E_{K+1}^{j+1} = E_{K+1}^j + \frac{\Delta t}{2\varepsilon_0 \Delta x}(H_{K+2}^j - H_{K,scattered}^j) =$$

$$E_{K+1}^j + \frac{\Delta t}{2\varepsilon_0 \Delta x}(H_{K+2}^j - (H_K^j - H_{inc}(x_K, t_j)))$$

where the differencing of total and incident quantities occurs first.

The H field is updated in substantially the same way. Using higher orders in space involves more points in the interface. For example, for $4^{th}$ order spatial derivatives, there 4 points in the transition region which have to be updated using analogues of (6) and (7).

In one embodiment, for any point, the derivative may be written as a combination of the left and the right derivatives (8):

$$\frac{\partial f}{\partial x} = \frac{1}{2}\left(\frac{\partial f}{\partial x_l} + \frac{\partial f}{\partial x_r}\right)$$

For i<K, the derivative is computed using spectral derivative on the total field (TF) region (302). For i>K+1, the derivative is computed using finite differences (FD) on the scattered field (304). Since there are only a few points, they may be very finely spaced. The spectral derivative is used for the left derivative and a right-handed stencil for the right derivative. To compute the transition region (306), the equation is (9):

$$E_K^{j+1} = E_K^j + \frac{1}{2}\frac{\Delta t}{2\varepsilon_0 \Delta x}(-H_{K+2,total}^j + 4H_{K+1,total}^j - 3H_K^j) + \frac{1}{2}\frac{\Delta t}{\varepsilon_0}\frac{\partial H_K^j}{\partial x_{spectral}} =$$

$$E_K^j + \frac{1}{2}\frac{\Delta t}{2\varepsilon_0 \Delta x}(-(H_{K+2}^j + H_{inc}(x_{K+2}, t_i)) +$$

$$4(H_{K+1}^j + H_{inc}(x_{K+1}, t_i)) - 3H_K^j) + \frac{1}{2}\frac{\Delta t}{\varepsilon_0}\frac{\partial H_K^j}{\partial x_{spectral}} =$$

$$E_K^j + \frac{1}{2}\frac{\Delta t}{2\varepsilon_0 \Delta x}(-(H_{K+2}^j) + 4(H_{K+1}^j) - 3H_K^j) + \frac{1}{2}\frac{\Delta t}{\varepsilon_0}\frac{\partial H_K^j}{\partial x_{spectral}} +$$

$$\frac{1}{2}\frac{\Delta t}{2\varepsilon_0 \Delta x}(-(H_{inc}(x_{K+2}, t_i)) + 4(H_{inc}(x_{K+1}, t_i)))$$

The last term in (9) allows for the injection of the incident field into the pseudo-spectral (PS) solve. For i=K+1, equation (7) continues to be used.

Accordingly, the matrix of coefficients is created using a combination of PS and FD methods. The incident field contributes solely to the right hand side of the matrix equation.

Non-Reflecting Boundary Conditions with Dispersion

In one embodiment of the present invention, the time-domain simulation uses non-reflecting boundary conditions so that the computational domain may be truncated. In stage 204 of FIG. 2, the solution of Maxwell's equations in the time domain may be used.

Figure 4:
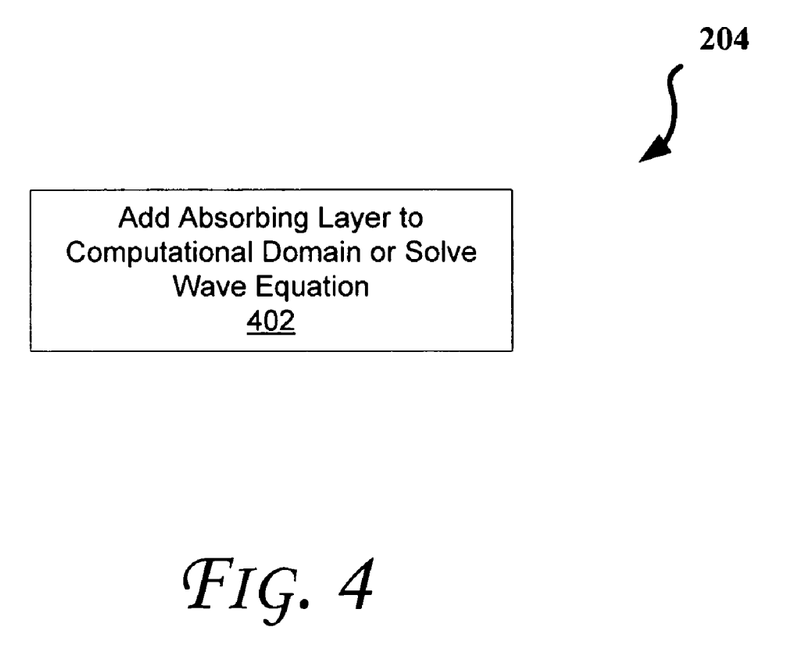

In one embodiment, an absorbing layer may be added to the computational domain or non-reflecting boundary conditions may be determined based on the solution the wave equation (402 of FIG. 4) to allow for the truncation of the computational domain. Several approaches may be used to form the non-reflecting boundary condition equations. The Perfectly Matched Layer (PML) is an alternative to non-reflecting boundary conditions based on the wave equation. In one embodiment, the non-reflecting boundary conditions may provide relatively smaller domains leading to smaller computational times.

In this alternative embodiment, the wave equation is given by (10):

$$\frac{\partial^2 u}{\partial t^2} = c^2 \frac{\partial^2 u}{\partial x^2}$$

from which the left traveling and the right traveling solutions (11) are obtained:

$$\frac{\partial u}{\partial t} \pm c \frac{\partial u}{\partial x} = 0$$

where the minus represents the right traveling solution and the plus the left traveling solution. Then, for example, for a right boundary, only the right traveling solutions are desired. Then an equation is determined for the update of the rightmost point $u_i$. After discretizing and using one-sided stencils for the derivatives, from (11):

$$\frac{u_i^{n+1} - u_i^n}{\Delta t} - c\frac{u_i^{n+1} - u_{i-1}^{n+1}}{\Delta x} = 0 \tag{12}$$

This yields (13):

$$u_i^{n+1} = \frac{1}{\Delta x - c\Delta t} \cdot (u_i^n \Delta x - u_{i-1}^{n+1} c \Delta t)$$

which is accurate to first order. Larger stencils may be used for the derivatives to obtain results accurate to higher order.

Since outgoing waves could travel in a variety of directions, thus prohibiting the simple use of (11) for a single preferred direction, the equation may be solved using the Fourier space of the directions parallel to the planar boundary. Thus, for three dimensions an analogous expression to (11) is given by (14):

$$\pm \frac{\partial u}{\partial x}(x, \eta, \zeta, t) + \frac{\partial u}{\partial t}(x, \eta, \zeta, t) + [\tau_w * u](x, \eta, \zeta, t) = 0$$

where $\tau_w$ is the plane convolution kernel which is applied using recursive accumulators. The derivatives, in analogy to (11), are given by one-handed derivative stencils and may be solved for the update variable.

These annihilation operators are based on the existence of the wave equation in the time domain. For dispersive materials this may not be the case, as pulses of the form f(x−ct) will not be Eigen functions of the operator and may undergo dispersion for any choice of c.

Starting in the frequency domain, Maxwell's equations are given by (15):

$$i\omega H(x, \omega) = \frac{\partial E}{\partial x}(x, w)$$

$$i\omega\varepsilon(\omega)E(x, \omega) = \frac{\partial H}{\partial x}(x, \omega)$$

This assumes the dielectric constant does not vary parallel to the plane boundary or for several cells (the size of the stencil) perpendicular to it. Thus, (16):

$$-\omega^2\varepsilon(\omega)E(x, \omega) = \frac{\partial^2 E}{\partial x^2}$$

This equation has two solutions given by (17):

$$E(x,\omega)=A(\omega)\exp(-i\omega\sqrt{\varepsilon(\omega)}\cdot x)+B(\omega)\exp(+i\omega\sqrt{\varepsilon(\omega)}\cdot x)$$

The above equation may be rewritten using $\sqrt{\varepsilon(\omega)}=n(\omega)+ik(\omega)$ to get (18):

$$E(x,\omega)=A(\omega)\exp((-i\omega n+\omega k)\cdot x)+B(\omega)\exp((i\omega n-\omega k)\cdot x)$$

The represents the left traveling and the right traveling solutions respectively. Thus, what is obtained is in analogy with (11) in the frequency domain (19):

$$\frac{\partial u}{\partial x}(x, \omega) \pm i\omega(n(\omega) + ik(\omega))u(x, \omega) = 0$$

The time domain dispersive kernel (20) may be defined:

$$\chi_1(t)=F^{-1}((n(\omega)+ik(\omega)))$$

Then, in the time domain (21):

$$\frac{\partial u}{\partial x}(x, t) \pm \left(\left[\chi_1 * \frac{\partial u}{\partial t}\right](x, t)\right) = 0$$

where the convolution may be computed using the recursive accumulator approach and the x-derivative may be computed using a one-handed stencil of appropriate order.

Using left traveling equation as an example and computing the spatial derivative to second order, (22):

$$\frac{(11u_i^{n+1} - 18u_{i-1}^{n+1} + 9u_{i-2}^{n+1} - 2u_{i-3}^{n+1})}{6\Delta x} +$$

$$\sum p_j \int_0^{t+\Delta t} e^{-s_j(t+\Delta t-\tau)}\frac{\partial u}{\partial t}(x_i, \tau)d\tau + \varepsilon_\infty\frac{\partial u}{\partial t}(x_i, t) = 0$$

where the special susceptibility is represented as a sum exponentials.

Thus, (23):

$$p_j\int_0^{t+\Delta t} e^{-s_j(t+\Delta t-\tau)}\frac{\partial u}{\partial t}(x_i, \tau)dt =$$

$$p_j\int_0^{t} e^{-s_j(t+\Delta t+\tau)}\frac{\partial u}{\partial t}(x_i, \tau)d\tau + p_j\int_t^{t+\Delta t} e^{-s_j(t+\Delta t-\tau)}\frac{\partial u}{\partial t}(x_i, \tau)d\tau =$$

$$\psi_j(t + \Delta t) = e^{-s_j\Delta t}\psi_j(t) + p_j\int_t^{t+\Delta t} e^{-s_j(t+\Delta t-\tau)}\frac{\partial u}{\partial t}(x_i, \tau)d\tau$$

The last integral is a very thin integral. The variable u may be approximated as a linear function on this integral for this treatment (higher order polynomials may be used, if desired). Then (24)

$$p_j\int_t^{t+\Delta t} e^{-s_j(t+\Delta t-\tau)}\frac{\partial u}{\partial t}(x_i, \tau)d\tau = p_j\left(\left(\frac{s_j\Delta t - 1 + e^{-s_j\Delta t}}{s_j^2\Delta t}\right)\right)\frac{\partial u_i^{n+1}}{\partial t} +$$

$$p_j\left(\frac{(1 - e^{-s_j\Delta t})}{s_j} - \left(\frac{s_j\Delta t - 1 + e^{-s_j\Delta t}}{s_j^2\Delta t}\right)\right)\frac{\partial u_i^n}{\partial t}$$

By definition, (25):

$$\chi_0^j = p_j\left(\frac{(1 - e^{-s_j\Delta t})}{s_j}\right) \text{ and}$$

$$\xi_0^j = p_j\left(\frac{(1 - e^{-s_j\Delta t})}{s_j} - \left(\frac{s_j\Delta t - 1 + e^{-s_j\Delta t}}{s_j^2\Delta t}\right)\right)$$

This yields (26) from (21):

$$\frac{(11u_i^{n+1} - 18u_{i-1}^{n+1} + 9u_{i-2}^{n+1} - 2u_{i-3}^{n+1})}{6\Delta x} +$$

$$\sum e^{-s_j\Delta t}\psi_j^n + \frac{\partial u_i^{n+1}}{\partial t}\left(\varepsilon_\infty + \sum(\chi_0^j - \xi_0^j)\right) + \frac{\partial u_i^n}{\partial t}\sum \xi_0^j = 0$$

Using a finite difference for the derivatives yields (27):

$$\frac{(25u_i^{n+1} - 48u_{i-1}^{n+1} + 36u_{i-2}^{n+1} - 16u_{i-3}^{n+1} + 3u_{i-4}^{n+1})}{12\Delta x} + \sum e^{-s_j\Delta t}\psi_j^n +$$

$$\frac{3u_i^{n+1} - 4u_i^n + u_i^{n-1}}{2\Delta t}\left(\varepsilon_\infty + \sum(\chi_0^j - \xi_0^j)\right) + \frac{u_i^{n+1} - u_i^{n-1}}{2\Delta t}\sum \xi_0^j = 0$$

Solving for u, the final form for the update equation (27) is:

$$u_i^{n+1} = \frac{-1}{\frac{25}{12\Delta x} + \frac{3(\varepsilon_\infty + \sum(\chi_0^j - \xi_0^j)) + \sum \xi_0^j}{2\Delta t}}\left[\sum e^{-s_j\Delta t}\psi_j^n + \right.$$

$$u_i^n\frac{-2(\varepsilon_\infty + \sum(\chi_0^j - \xi_0^j))}{\Delta t} - u_i^{n-1}\frac{\frac{1}{2}\sum \xi_0^j - \frac{1}{2}(\varepsilon_\infty + \sum(\chi_0^j - \xi_0^j))}{\Delta t} +$$

$$\left.\frac{-48u_{i-1}^{n+1} + 36u_{i-2}^{n+1} - 16u_{i-3}^{n+1} + 3u_{i-4}^{n+1}}{12\Delta x}\right]$$

In an embodiment, one of the advantages of this method is that no additional cells are introduced and the cost of updating the special boundary points may be comparable to the cost of updating interior points in a dispersive material.

In two dimensions (28):

$$i\omega H_z(x, y, \omega) = -\frac{\partial E_y}{\partial x}(x, y, w) + \frac{\partial E_x}{\partial y}(x, y, w)$$

-continued $$i\omega\varepsilon(\omega)E_x(x, y, \omega) = \frac{\partial H_z}{\partial y}(x, y, \omega)$$

$$i\omega\varepsilon(\omega)E_y(x, y, \omega) = -\frac{\partial H_z}{\partial x}(x, y, \omega)$$

Using a Fourier transform with respect to y yields (29):

$$i\omega H_z(x, \zeta, \omega) = -\frac{\partial E_y}{\partial x}(x, \zeta, w) + i\zeta E_x(x, \zeta, w)$$

$$i\omega\varepsilon(\omega)E_x(x, \zeta, \omega) = i\zeta H_z(x, \zeta, \omega)$$

$$i\omega\varepsilon(\omega)E_y(x, \zeta, \omega) = -\frac{\partial H_z}{\partial x}(x, \zeta, \omega)$$

Eliminating the E-fields, an equation for Hz only may be given by (30):

$$-\omega^2\varepsilon(\omega)H_z(x, \zeta, \omega) = \frac{\partial^2 H_z}{\partial x^2}(x, \zeta, w) - \zeta^2 H_z(x, \zeta, w)$$

From which we get (22):

$$(\zeta^2 - \omega^2\varepsilon(\omega))H_z(x, \zeta, \omega) = \frac{\partial^2 H_z}{\partial x^2}(x, \zeta, w)$$

This equation is in analogy with (16). Similarly to (17), an equation describing left and right traveling waves (31):

$$H(x, \zeta, \omega) =$$
$$A(\omega)\exp\left(-i\omega\sqrt{\varepsilon(\omega) - \frac{\zeta^2}{\omega^2}} \cdot x\right) + B(\omega)\exp\left(+i\omega\sqrt{\varepsilon(\omega) - \frac{\zeta^2}{\omega^2}} \cdot x\right)$$

In analogy with (20), time-domain non-reflecting boundary condition susceptibility is defined by function (32):

$$\chi_1(t, \zeta) = F^{-1}\left(\sqrt{\varepsilon(\omega) - \frac{\zeta^2}{\omega^2}}\right)$$

This yields an equation similar to (21) in two dimensions given by (33):

$$\frac{\partial u}{\partial x}(x, \zeta, t) \pm \left(\left[\chi_1 * \frac{\partial u}{\partial t}\right](x, \zeta, t)\right) = 0$$

The application of equations (22)-(27) is identical except for the use of the two dimension time-domain non-reflecting susceptibility function.

Now that the derivation of the two dimensional non-reflecting boundary condition is completed, the three dimensional condition may be determined by inspection. In three dimensions, instead of (32), what is generated is (35):

$$H(x, \zeta, \eta, \omega) =$$
$$A(\omega)\exp\left(-i\omega\sqrt{\varepsilon(\omega) - \frac{\zeta^2 + \eta^2}{\omega^2}} \cdot x\right) + B(\omega)\exp\left(+i\omega\sqrt{\varepsilon(\omega) - \frac{\zeta^2 + \eta^2}{\omega^2}} \cdot x\right)$$

Where $\eta$ and $\zeta$ are conjugate variables with respect to y and z. Equation (34) becomes (36):

$$\frac{\partial u}{\partial x}(x, \zeta, \eta, t) \pm \left(\left[\chi_1 * \frac{\partial u}{\partial t}\right](x, \zeta, \eta, t)\right) = 0$$

The rest of the computation follows the (22)-(27) of the one-dimensional derivation above.

Figure 5:
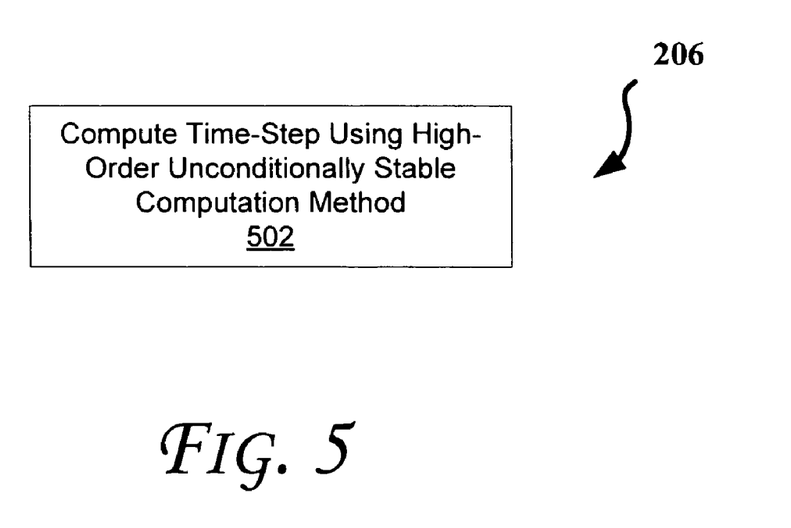

As shown in FIG. 5, stage 206 uses a high-order unconditionally stable computation method which is both stable and accurate for large time-steps. In one embodiment of stage 206, the time-step is computed using the standard Alternate Direction Implicit time-stepping method (ADI) with a full time step $\Delta t$ advancing from time step n to time step n+1, is described by the following stepping equations which advance the state vector in two substeps $$\frac{\Delta t}{2},$$

each having an implicit and an explicit part:

$$\left(1 - \frac{\Delta t}{2}A\right)w^{(n+\frac{1}{2})} = \left(1 + \frac{\Delta t}{2}B\right)w^{(n)} \quad (37a)$$

$$\left(1 - \frac{\Delta t}{2}B\right)w^{(n+1)} = \left(1 + \frac{\Delta t}{2}A\right)w^{(n+\frac{1}{2})} \quad (37b)$$

This method is of second order in time (as will be shown later).

If equation (37a) is multiplied by $$\left(1 + \frac{\Delta t}{2}A\right)$$

and equation (37b) by $$\left(1 - \frac{\Delta t}{2}A\right),$$

then add the two up and use the fact that $$\left(1 + \frac{\Delta t}{2}A\right) \text{ and } \left(1 - \frac{\Delta t}{2}A\right)$$

commute, the full step ADI equation is obtained:

$$\left(1 - \frac{\Delta t}{2}A\right)\left(1 - \frac{\Delta t}{2}B\right)w^{(n+1)} = \left(1 + \frac{\Delta t}{2}A\right)\left(1 + \frac{\Delta t}{2}B\right)w^{(n)} \quad (38)$$

The following embodiments describe various methods for increasing the order in time of ADI from $2^{nd}$ to $4^{th}$ and higher order.

In one embodiment, the power series approach may raise ADI order in time, at a very low cost.

In another embodiment, the Split-step method may be used to raise ADI order in time, at a cost of 3× (cost of ADI) for $4^{th}$ order or 7× (cost of ADI) for $6^{th}$ order.

In another embodiment, the Deferred Correction Method (DCM) may raise ADI order in time, at a cost of (roughly) 2× (cost of ADI) for $4^{th}$ order or 3× (cost of ADI) for $6^{th}$ order.

The DCM primarily is used to run $2^{nd}$ order ADI over a possibly large number of steps, then to use the fields thus obtained to compute $3^{rd}$ order corrections at each step, and re-run ADI while adding these corrections at each sub-step.

Assuming that the $2^{nd}$ order ADI needs a correction C at each full step in order to become higher order, equation (38) becomes:

$$\left(1 - \frac{\Delta t}{2}A\right)\left(1 - \frac{\Delta t}{2}B\right)w^{(n+1)} = \left(1 + \frac{\Delta t}{2}A\right)\left(1 + \frac{\Delta t}{2}B\right)w^{(n)} + C \quad (39)$$

The correction would then be given by:

$$C = \left(1 - \frac{\Delta t}{2}A\right)\left(1 - \frac{\Delta t}{2}B\right)w^{(n+1)} - \left(1 + \frac{\Delta t}{2}A\right)\left(1 + \frac{\Delta t}{2}B\right)w^{(n)} = \quad (40)$$

$$\left(1 + \frac{\Delta t^2}{4}AB\right)(w^{(n+1)} - w^{(n)}) - \frac{\Delta t}{2}(A+B)(w^{(n+1)} + w^{(n)})$$

The state vector difference and sum may be expanded Taylor series, taking advantage of the fact that these may contain only the odd or even terms, respectively:

$$w^{(n+1)} - w^{(n)} = \Delta t \frac{\partial w^{(n+\frac{1}{2})}}{\partial t} + \frac{\Delta t^3}{24}\frac{\partial^3 w^{(n+\frac{1}{2})}}{\partial t^3} + \frac{\Delta t^5}{1920}\frac{\partial^5 w^{(n+\frac{1}{2})}}{\partial t^5} + \ldots \quad (40a)$$

$$w^{(n+1)} + w^{(n)} = 2w^{(n+\frac{1}{2})} + \frac{\Delta t^2}{4}\frac{\partial^2 w^{(n+\frac{1}{2})}}{\partial t^2} + \frac{\Delta t^4}{192}\frac{\partial^4 w^{(n+\frac{1}{2})}}{\partial t^4} + \ldots \quad (40b)$$

Substituting into the correction expression:

$$C = \left(\frac{\partial w^{(n+\frac{1}{2})}}{\partial t} - (A+B)w^{(n+\frac{1}{2})}\right)\Delta t + \quad (41)$$

$$\left(\frac{1}{4}AB\frac{\partial w^{(n+\frac{1}{2})}}{\partial t} - \frac{(A+B)}{8}\frac{\partial^2 w^{(n+\frac{1}{2})}}{\partial t^2} + \frac{1}{24}\frac{\partial^3 w^{(n+\frac{1}{2})}}{\partial t^3}\right)\Delta t^3 +$$

$$\left(\frac{AB}{96}\frac{\partial^3 w^{(n+\frac{1}{2})}}{\partial t^3} - \frac{(A+B)}{384}\frac{\partial^4 w^{(n+\frac{1}{2})}}{\partial t^4} + \frac{1}{1920}\frac{\partial^5 w^{(n+\frac{1}{2})}}{\partial t^5}\right)\Delta t^5 + \ldots$$

In (41), the $1^{st}$ order of the correction is identically 0 because of the original Maxwell equation, and there is no $2^{nd}$ order term, thus confirming that ADI is $2^{nd}$ order accurate in time.

In order to get a $4^{th}$ order accurate method, it is enough to compute accurately enough and then use the $3^{rd}$ order term in (41), since there is no $4^{th}$ order term in the correction.

A particularly elegant way to compute the time derivatives of w is by repeated central differences:

$$\frac{\partial w^{(n+\frac{1}{2})}}{\partial t} \approx \frac{w^{(n+1)} - w^{(n)}}{\Delta t} \quad (42)$$

$$\frac{\partial^2 w^{(n+\frac{1}{2})}}{\partial t^2} \approx \frac{w^{(n+2)} - w^{(n+1)} - w^{(n)} + w^{(n-1)}}{2\Delta t^2}$$

$$\frac{\partial^3 w^{(n+\frac{1}{2})}}{\partial t^3} \approx \frac{w^{(n+2)} - 3w^{(n+1)} + 3w^{(n)} - w^{(n-1)}}{\Delta t^3}$$

Substituting these finite differences into (41), we get the expression of the correction needed in order to raise the accuracy in time to $4^{th}$ order:

$$C \approx \quad (43)$$

$$\frac{\Delta t^2}{4}AB(w^{(n+1)} - w^{(n)}) - \frac{\Delta t}{16}(A+B)(w^{(n+2)} - w^{(n+1)} - w^{(n)} + w^{(n-1)}) +$$

$$\frac{1}{24}(w^{(n+2)} - 3w^{(n+1)} + 3w^{(n)} - w^{(n-1)})$$

Thus, after computing the correction in (43) based on the first run of ADI, ADI is run again but this time applying half the correction at each time sub-step:

$$\left(1 - \frac{\Delta t}{2}A\right)w^{(n+\frac{1}{2})} = \left(1 + \frac{\Delta t}{2}B\right)w^{(n)} + \frac{C}{2} \quad (44a)$$

$$\left(1 - \frac{\Delta t}{2}B\right)w^{(n+1)} = \left(1 + \frac{\Delta t}{2}A\right)w^{(n+\frac{1}{2})} + \frac{C}{2} \quad (44b)$$

This symmetrical application of half the correction at each sub-step is equivalent to the application of the full correction after the full step, as can be verified by multiplying equation (44a) by $$\left(1 + \frac{\Delta t}{2}A\right)$$

and equation (44b) by $$\left(1 - \frac{\Delta t}{2}A\right),$$

then add the two up and use the fact that $$\left(1 + \frac{\Delta t}{2}A\right) \text{ and } \left(1 - \frac{\Delta t}{2}A\right)$$

commute.

The DCM offers a way to raise the accuracy of ADI to $4^{th}$ order. If a $6^{th}$ order time accuracy turns out to be needed, a similar calculation of the $5^{th}$ order correction is needed, based on the $4^{th}$ order accurate state vectors computed in the second run of ADI. This correction may then be applied during a $3^{rd}$ run of ADI.

Field Transformation

In cases of oblique incidence, a field transformation maybe used to transform the problem from an extended domain into a problem with a periodic domain. In that case the equations are slightly modified from Maxwell's equations. The new equations are given in the 2D TE case by:

$$\frac{1}{c}\frac{\partial Q_z}{\partial t} = -\frac{\partial P_y}{\partial x} + \frac{\sin\theta}{c}\frac{\partial P_y}{\partial t}$$

$$\frac{1}{c}\frac{\partial Q_x}{\partial t} = \frac{\partial P_y}{\partial z}$$

$$\frac{\varepsilon(x,z)}{c}\frac{\partial P_y}{\partial t} = \frac{\partial Q_z}{\partial z} - \frac{\partial Q_z}{\partial x} + \frac{\sin\theta}{c}\frac{\partial Q_z}{\partial t}$$

This new set of equation may be solved by exactly the same techniques as the original set of Maxwell's equation. If an explicit, conditionally stable time-stepping method is used; however, a relatively very small time step may be required to obtain stability. In one embodiment, where an unconditionally stable time-stepping method is used—the time step utilized may be relatively large and, thus, significantly improve the computation time.

In the description and claims, the terms "coupled" and "connected," along with their derivatives, may be used. In some embodiments of the invention, "connected" may be used to indicate that two or more elements are in direct physical contact with each other. "Coupled" may mean that two or more elements are in direct physical contact. However, "coupled" may also mean that two or more elements may not be in direct contact with each other, but may still cooperate or interact with each other.

Although embodiments have been described in language specific to structural features and/or methodological acts, it is to be understood that claimed subject matter may not be limited to the specific features or acts described. Rather, the specific features and acts are disclosed as sample forms of implementing various embodiments. While the invention has been described above in conjunction with one or more specific embodiments, it should be understood that the invention is not intended to be limited to one embodiment. The invention is intended to cover alternatives, modifications, and equivalents as may be included within the spirit and scope of the invention, such as those defined by the appended claims.

What is claimed is:

1. A method of time-domain computation for simulating electromagnetic (EM) scattering spectra comprising:
   a processor computing spatial derivatives comprising computing spectral derivatives in some portion of the domain and finite difference derivatives in some other portion of the domain;
   the processor forming an equation for boundary conditions; and
   the processor computing a time-stepping scheme.

2. The method of claim 1, further comprising computing spatial derivatives of a transition portion of the domain using a linear combination of the spectral derivatives and finite difference derivatives.

3. The method of claim 1, wherein forming the equation for boundary conditions comprises forming the equation for non-reflecting boundary conditions to truncate the computational domain.

4. The method of claim 3, further comprising adding an absorbing layer to the computational domain.

5. The method of claim 3, wherein forming the equation for non-reflecting boundary conditions comprises computing a solution to a wave equation.

6. The method of claim 1, wherein computing the time-stepping scheme comprises computing the time-stepping using a high-order unconditionally stable computation method.

7. The method of claim 1, wherein materials under simulation have frequency-dependent dispersive dielectric properties.

8. The method of claim 1, wherein the time-stepping scheme comprises a field transformed system of equations for oblique incidence on a periodic domain.

9. The method of claim 1, further comprising computing a linear combination of plane waves for an incident pulse to simulate a finite aperture for the incident pulse in a single time-domain solution.

10. A method of time-domain computation for simulating electromagnetic (EM) scattering spectra comprising:
    a processor computing spatial derivatives of the domain;
    the processor forming an equation for non-reflecting boundary conditions to truncate the computational domain; and
    the processor computing a time-stepping scheme.

11. The method of claim 10, wherein computing spatial derivatives of the domain comprises computing spectral derivatives in some portion of the domain and finite difference derivatives in some other portion of the domain.

12. The method of claim 10, further comprising computing spatial derivatives of a transition portion of the domain using a linear combination of the spectral derivatives and finite difference derivatives.

13. The method of claim 10, wherein forming the equation for non-reflecting boundary conditions comprises computing a solution to a wave equation.

14. The method of claim 10, wherein computing the time-stepping scheme comprises computing the time-stepping using a high-order unconditionally stable computation method.

15. The method of claim 10, wherein materials under simulation comprise frequency-dependent dispersive dielectric properties.

16. The method of claim 10, wherein the time-stepping scheme comprises a field transformed system of equations for oblique incidence on a periodic domain.

17. A method of time-domain computation for simulating electromagnetic (EM) scattering spectra comprising:
    a processor computing spatial derivatives of the domain;
    the processor forming an equation for boundary conditions; and
    the processor computing a time-stepping scheme using a high-order unconditionally stable computation method.

18. The method of claim 17, wherein computing spatial derivatives of the domain comprises computing spectral derivatives in some portion of the domain and finite difference derivatives in some other portion of the domain.

19. The method of claim 17, further comprising computing spatial derivatives of a transition portion of the domain using a linear combination of the spectral derivatives and finite difference derivatives.

20. The method of claim 17, wherein forming the equation for boundary conditions comprises forming the equation for non-reflecting boundary conditions to truncate the computational domain.

21. The method of claim 20, wherein forming the equation for non-reflecting boundary conditions comprises computing a solution to a wave equation.

22. A system for measuring electromagnetic (EM) spectra and computing a time-domain simulation for simulating scattering spectra comprising:
- a broadband EM radiation source for illuminating a wafer;
- a spectrometer to detect different spectral components of radiation reflected from the wafer; and
- a processor to compute scattering spectra by:
  - computing spatial derivatives comprising computing spectral derivatives in some portion of the domain and finite difference derivatives in some other portion of the domain;
  - forming an equation for non-reflecting boundary conditions;
  - computing a high-order unconditionally stable computation method;
  - varying the model geometry; and
  - re-computing the computed scattering spectra until the computed scatting spectra matches a measured spectrum.

23. The system of claim 22, wherein the processor computes scattering spectra by computing spatial derivatives of a transition portion of the domain using a linear combination of the spectral derivatives and finite difference derivatives.

24. The system of claim 22, wherein materials under simulation comprise frequency-dependent dispersive dielectric properties.

25. The system of claim 22, wherein the processor computes scattering spectra by computing spatial derivatives of a transition portion of the time-domain using a linear combination of the spectral derivatives and finite difference derivatives.

26. The system of claim 22, wherein the time-domain under computation comprises a time-domain of finite extent.

27. The system of claim 22, wherein the time-domain under computation comprises a periodic domain.

28. The system of claim 22, wherein the processor computes a field transformed system of equations for oblique incidence on a periodic domain.

* * * * *